United States Patent [19]

Bach et al.

[11] Patent Number: 4,553,254

[45] Date of Patent: Nov. 12, 1985

[54] X-RAY DIAGNOSTIC SYSTEM COMPRISING AT LEAST ONE X-RAY GENERATOR AND X-RAY APPARATUS

[75] Inventors: Eric Bach, Spardorf; Dieter Schmidt, Hetzles, both of Fed. Rep. of Germany

[73] Assignee: Siemens Aktiengesellschaft, Berlin & Munich, Fed. Rep. of Germany

[21] Appl. No.: 564,915

[22] Filed: Dec. 23, 1983

Related U.S. Application Data

[63] Continuation of Ser. No. 299,147, Sep. 3, 1981.

[30] Foreign Application Priority Data

Sep. 16, 1980 [DE] Fed. Rep. of Germany ....... 3034933

[51] Int. Cl.[4] .............................................. A61B 6/00

[52] U.S. Cl. ...................................... 378/098; 378/92; 378/116

[58] Field of Search .................... 378/92, 115, 116, 98

[56] References Cited

U.S. PATENT DOCUMENTS

| | | | |
|---|---|---|---|
| 3,775,560 | 11/1973 | Ebeling et al. | 178/18 |
| 4,037,107 | 7/1977 | Lutz et al. | 378/092 |
| 4,079,450 | 3/1978 | Grimm et al. | 364/200 |
| 4,158,138 | 6/1979 | Hellstrom | 378/116 |
| 4,251,729 | 2/1981 | Pfeifer | 378/116 |

FOREIGN PATENT DOCUMENTS

| | | |
|---|---|---|
| 2057997 | 6/1972 | Fed. Rep. of Germany . |
| 2323710 | 11/1974 | Fed. Rep. of Germany . |
| 2399182 | 2/1979 | France . |
| 1463198 | 2/1977 | United Kingdom . |

*Primary Examiner*—Alfred E. Smith
*Assistant Examiner*—T. N. Grigsby
*Attorney, Agent, or Firm*—Hill, Van Santen, Steadman & Simpson

[57] ABSTRACT

An exemplary embodiment includes x-ray apparatus and auxiliary apparatus, such as a sheet film camera or an image intensifier television chain, as well as comprising operating consoles for generator and apparatus control. The operating consoles are intelligent data display apparatus which are connected to a central computer unit which controls the x-ray generator and the x-ray apparatus and which effects the display of data of the x-ray diagnostic system on the data display apparatus. The data display apparatus are provided with a matrix arrangement for the purpose of data input through manual contacting of the display screen at a location corresponding to a desired input.

2 Claims, 1 Drawing Figure

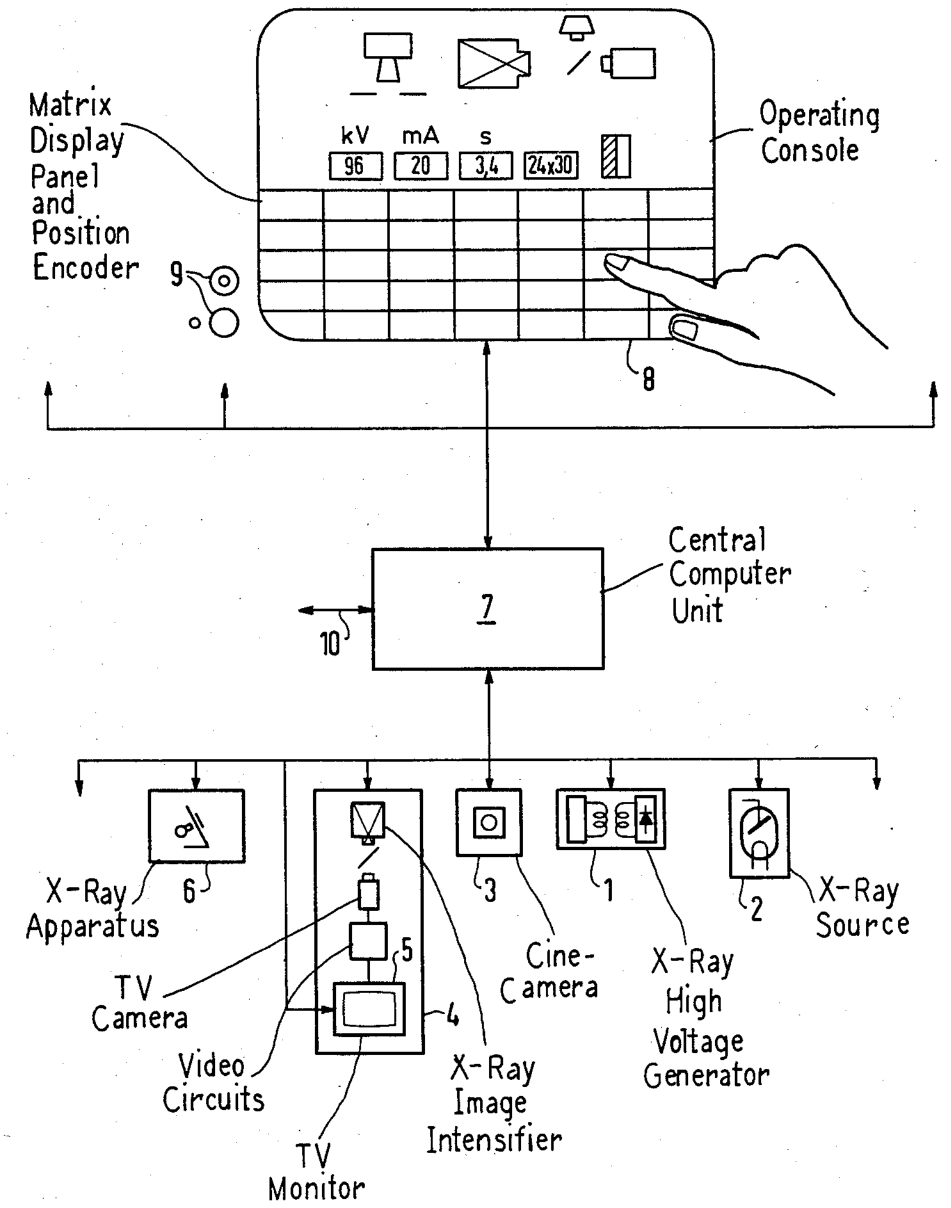
Matrix Display Panel and Position Encoder
Operating Console
kV
mA
s
96
20
3,4
24x30
9
8
Central Computer Unit
7
10
X-Ray Apparatus
6
TV Camera
Video Circuits
TV Monitor
5
4
X-Ray Image Intensifier
3
Cine-Camera
1
X-Ray High Voltage Generator
2
X-Ray Source

X-RAY DIAGNOSTIC SYSTEM COMPRISING AT LEAST ONE X-RAY GENERATOR AND X-RAY APPARATUS

This is a continuation, of application Ser. No. 299,147, filed Sept. 3, 1981.

BACKGROUND OF THE INVENTION

The invention relates to an x-ray diagnostic system comprising at least one x-ray generator, x-ray apparatus, and auxiliary apparatus, such as a sheet film camera or an image intensifier television chain, as well as comprising operating consoles for generator and apparatus control.

In the case of known x-ray diagnostic systems of this type, the operating consoles are provided with keys which render possible the input of data for the adjustment of the x-ray generator and control of the x-ray apparatus. For each x-ray apparatus an individually matched console is additionally present which can be expanded by additional consoles for auxiliary apparatus. This signifies that, for an x-ray diagnostic system, several differently designed operating consoles must be present.

SUMMARY OF THE INVENTION

The object underlying the invention resides in producing an x-ray diagnostic system of the type initially cited in which it is possible to employ a uniform operating console.

In accordance with the invention, this object is achieved in that the operating consoles are intelligent data display devices which are connected to a central computer unit, the central computer unit controlling the x-ray generator and the x-ray apparatus, and effecting the display of data pertaining to the x-ray diagnostic system on the data display apparatus of each console after the data has been obtained from the operating console by the computer, and in that the data display apparatus is provided with means for data input to the computer by manual contacting of the display screen at corresponding data transmitting locations thereof. In the case of the inventive x-ray diagnostic system, an operating console with a display screen is provided on which, through switching on of the operating console, an established data program is displayed with the aid of the computer unit. The displayed data categories appear at specific locations of the display screen and, through manual contacting, in dependence upon the contacting point, data can be input into the computer unit which, in turn, correspondingly controls the x-ray apparatus and the x-ray generator, or displays corresponding subprograms. Thus, for example, it is possible, for a specific work place, through contacting of the display screen of the associated data display apparatus, to adjust the x-ray tube voltage and the x-ray tube current, to select the radiation sensing region of the automatic exposure timer which is to be dominant, etc. Each operating console is here universally employable, since the displayed data is determined only by the central computer unit.

The operating design in accordance with the invention can be uniformly employed in all x-ray diagnostic systems. An organ-related central operation and the guidance of the operator in the selection of operating parameters (executive programs and subprograms) facilitate the system operation.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWING

The single FIGURE is a diagrammatic illustration of an exemplary embodiment in accordance with the present invention.

DETAILED DESCRIPTION

In the drawing, an x-ray diagnostic system is illustrated including an x-ray high voltage generator 1, an x-ray radiator 2, a cine camera 3 for display screen photography, an image intensifier television chain 4 of an x-ray apparatus including a television monitor 5 of the image intensifier television chain 4, as well as an x-ray apparatus 6, for example a motor-driven tilting table type of apparatus as described in the Siemens brochure Order No. 12/7167.101 of December 1976. From the components 1 through 6, data lines lead to a central computer unit 7 which may be a microcomputer system. As part of the microcomputer system several operating consoles, corresponding to the provided components, are connected, of which one is illustrated and referenced with 8. From the operating consoles, data lines likewise lead to the microcomputer. The operating consoles are intelligent data display apparatus from which a dialog with the computer unit 7 is possible. If, for example, the operating console 8 is switched on by means of a switch 9, first an executive program from the computer unit 7 is called up and displayed on the display screen of the operating console 8. On the basis of the displayed executive program it is now possible, through contacting of specific locations of the display screen of the operating console 8, to input specific data and to render possible their adjustment. If, for example, a field representing a specific dominant of an automatic exposure timer is contacted, then this dominant is selected via the computer unit 7. An additional example is that, through contacting of a specific location of the display screen of the operating console 8, the setpoint value for the dose rate of the image intensifier television chain 4, which is provided with a dose rate control installation, can be selected. In addition, it is possible, through contacting of the display screen of the operating console 8, to call up subprograms.

The scanning to determine the respective position of the contact point for the purpose of data input can occur in a known fashion, for example, with the aid of infrared light radiation, which radiates in matrix-fashion over the display screen of the operating console 8, and which is interrupted at a specific location with the aid of the finger of the operator, such as is described, for example, in U.S. Pat. No. 3,775,560.

Via a data bus 10, a data transmission to a remote station, for example, for statistical purposes, is possible.

It will be apparent that many modifications and variations may be effected without departing from the scope of the novel concepts and teachings of the present invention.

Supplementary Discussion

In order to provide a more specific understanding of the functioning of the illustrated system, an example of an operating sequence will be set forth below, having reference to the previously referenced x-ray apparatus of the general type described in the brochure Order No. 12/7167.101.

When the operating console 8 is activated, e.g. by a switch 9, the computer 7 may be signalled with a code identifying the particular console, the console with such identifying code having previously been assigned particular programming appropriate to the associated equipment. Thus for the particular case illustrated in the drawing, the computer may illuminate a column of the matrix display panel with printed indicia, requesting information as to the particular type of operation desired, for example "Fluoroscopy" by means of the television chain 4, "Spotfilm" operation using an overtable spotfilm device, or "Serial Camera" using a serial camera 3 in conjunction with the image intensifier of the assembly 4. The first three positions of the left hand column thus may be permanently assigned the categories "Fluoroscopy", "Spotfilm", and "Serial Camera", for example by means of a transparent overlay sheet covering the thirty-five locations of the matrix display panel, and having respective legends printed thereon which can be selectively illuminated by individual visible light sources controlled by computer 7 to selectively project visible light onto the respective matrix locations.

The computer 7 having acknowledged activation of the specific operating console 8 shown in the drawing, (e.g. by illuminating the legends at the left or first column of the matrix panel), the operator may press the second illuminated location of the first column, signifying that a spotfilm operation is desired.

For the case of selection of a spotfilm operation, the first two locations of the second, third and fourth columns may be illuminated and all of the fifth and sixth columns may be illuminated while only the second location of the first column remains illuminated, signifying that the computer has received the "Spotfilm" selection and is ready to receive specific operating parameters for this type of an operation. Thus the first location of columns two, three and four may display a plus symbol indicating that when such a location is pressed, the x-ray tube voltage (kV), current (mA) or exposure time (s) will be incremented to increase the value displayed in a display region above the respective column. The second locations of columns two, three and four may have a minus symbol illuminated to signify that the displayed value will be decreased. Thus pressing the first location at column two may increase the voltage setting by a suitable increment, e.g. four kilovolts, so that the display region above column two would show a setting of 100 kV. Pressing the second location of column two once would then restore the value 96 kV, and pressing the location again could establish a value of e.g. 92 kV. Similar operation would result in columns three and four. In each case the computer 7 would be programmed to provide successive values of voltage, current and exposure time which were within preestablished proper operating limits, and within the capability of the associated x-ray source 2 and the available film of apparatus 6.

The fifth column could provide for a selection of film size, e.g. 18×24 cm, 24×30 cm, 30×30 cm and 35×35 cm. If the second location of the fifth column were pressed, the associated display would be "24×30" as shown on the drawing. The sixth column could select film format, e.g. "survey" or full field, "two-field", "three-field", "four-field" or "six-field". Pressing the second location of column six would produce the two field display, with the left field darkened, as shown in the drawing. After a first exposure, the right half of the two field would be shown darkened by the computer, and after the second exposure, the display could be an entirely light two-field display, signifying that a cassette change was required before a further exposure.

In place of printed indicia on a transparent overlay or the like and selectively energizable visible light sources, other means of computer communication with the operator at console 8 may be used, for example the plasma display panel of the referenced U.S. Pat. No. 3,775,560, solid state displays, and the like.

We claim as our invention:

1. An x-ray diagnostic system comprising at least one x-ray high voltage generator, x-ray apparatus and auxiliary apparatus, such as a sheet film camera or an image intensifier television chain, and operating consoles for generator and apparatus control, the operating consoles each comprising an intelligent data display apparatus having a display screen with data representing regions, a central computer unit which controls the x-ray high voltage generator and the x-ray apparatus and effects the display of data of the x-ray diagnostic system on the data display apparatus, the data display apparatus of each operating console being connected with the central computer unit and including means providing respective data transmitting locations associated with respective data representing regions of the display screen for the purpose of data input to the central computer unit through contacting of the display screen at selected data representing regions so as to actuate the corresponding data transmitting locations.

2. An x-ray diagnostic system according to claim 1, said display screen being in the form of a matrix display panel and position encoder, with said data transmitting locations being arranged in a matrix and the respective data transmitting locations of said matrix being responsive to selective contacting of respective ones of said data representing regions to produce a corresponding position code at said position encoder which is transmitted to said central computer, said data representing regions being controlled by said central computer unit to guide the operator at each operating console in communicating with said central computer unit.

* * * * *